United States Patent [19]

Inward

[11] Patent Number: 4,944,933
[45] Date of Patent: Jul. 31, 1990

[54] PREPARATION OF BASIC ALUMINIUM HALIDES

[75] Inventor: Peter W. Inward, Wirral, England

[73] Assignee: Lever Brothers Company, New York, N.Y.

[21] Appl. No.: 355,885

[22] Filed: May 19, 1989

Related U.S. Application Data

[63] Continuation of Ser. No. 30,194, Mar. 24, 1987, abandoned.

[30] Foreign Application Priority Data

Mar. 27, 1986 [GB] United Kingdom ............... 8707718
Aug. 11, 1986 [GB] United Kingdom ............... 8619551

[51] Int. Cl.$^5$ .............................................. C01F 7/56
[52] U.S. Cl. ..................................................... 423/462
[58] Field of Search ........................... 423/462; 424/68

[56] References Cited

U.S. PATENT DOCUMENTS

| | | | |
|---|---|---|---|
| 2,196,016 | 4/1940 | Huehn et al. | 423/462 |
| 3,476,509 | 11/1969 | Jones | 423/462 |
| 3,507,896 | 4/1970 | Jones et al. | 260/448 |
| 3,927,184 | 12/1975 | Hodgson | 423/394 |
| 4,359,456 | 11/1982 | Gasliag et al. | 423/462 |
| 4,818,512 | 4/1989 | Markarian et al. | 423/462 |
| 4,859,446 | 8/1989 | Abrutyn et al. | 423/462 |
| 4,871,525 | 10/1989 | Giovanniello et al. | 423/462 |

FOREIGN PATENT DOCUMENTS

| | | | |
|---|---|---|---|
| 150410 | 7/1951 | Australia . | |
| 191628 | 8/1986 | European Pat. Off. . | |
| 1319437 | 6/1973 | United Kingdom . | |
| 2048229 | 12/1980 | United Kingdom | 423/462 |

OTHER PUBLICATIONS

Chemistry, Bailar, Jr. et al., Academic Press, 1978, pp. 419–420, 736.
Article by Akitt et al. (J. C. S. Dalton Tranactions 1972, pp. 604 to p. 610).
Acta Chem. Scand., 1960, vol. 14 by G. Johansson, pp. 771–773.
Schönherr et al., Basic Aluminum Salts and Their Solutions, Z. Anorg. allg., 502, 113–122 (1983) (original plus translation).
Article by Akitt et al. (J. C. S. Dalton Transactions, 1981, pp. 1624–1628).

*Primary Examiner*—Jeffrey E. Russel
*Attorney, Agent, or Firm*—Gerard J. McGowan, Jr.

[57] ABSTRACT

The disclosure concerns a process for the manufacture of basic aluminium chlorides in powder form for antiperspirant use which have an aluminium:chloride molar ratio of 1.7:1 to 2.2:1 and has a Band III fraction of at least 20% as determined by a chromatographic procedure. The disclosure centers on the finding of advantageous reaction conditions for the known reaction between aluminium powder and an aqueous aluminium chloride solution. The temperature of reaction is 50° to 105° C. and the final aluminium concentration of the solution is 7.5% to 13%. It has been discovered that if this reaction is carried out sufficiently rapidly a solution of a basic aluminium chloride is produced having a Band III fraction of at least 20%. The disclosure shows the influence of the grade of aluminium and manner of conducting the reaction on reaction time. The solution obtained is dried, preferably spray dried or freeze dried, to give the powder.

9 Claims, No Drawings

PREPARATION OF BASIC ALUMINIUM HALIDES

This is a continuation, application of Ser. No. 030,194, filed Mar. 24, 1987, now abandoned.

This invention relates to the preparation of basic aluminium chlorides, more particularly to the preparation of a basic aluminium chloride in the form of a hydrated powder having good antiperspirant activity.

Basic aluminium chlorides have been available commercially for many years both in the form of aqueous solutions and in the form of hydrated powders. One well known application of these products is as the active ingredient of antiperspirant products. For such application the basic aluminium chlorides are commercially available in varying degrees of basicity, which can be expressed in terms of the aluminium to chlorine ratio. The powdered forms of the basic aluminium chlorides are frequently obtained by spray-drying aqueous solutions of the basic chlorides. These solutions are usually made by dissolving aluminium metal in an aqueous solution of aluminium chloride at an elevated temperature and such method is described in U.S. Pat. No. 2,196,016 (Huehn et al) and AU-A-No. 150,410 (Elliotts & Australian Drug Proprietary Ltd). The amount of aluminium metal dissolved is controlled so as to correspond to a final product having the desired aluminium to chlorine ratio. Furthermore, the concentration of the aluminium chloride solution is chosen so as to give a final product having an aluminium concentration of around 12% by weight which is most advantageous for commercial sale or for conversion to a powdered form, e.g. by spray drying such solutions.

In U.S. Pat. No. 4,359,456 (Gosling et al), the disclosure of which is incorporated herein by reference, there is described a process for making from commercially available materials a basic aluminium chloride having enhanced antiperspirant efficacy. The process described by the prior patent involves first forming a solution of the basic aluminium chloride having an aluminium concentration of 2.5 to 8.5% by weight. This can be prepared by dissolving in water a commercially available powder of a basic aluminium chloride (as in Example 2) or by diluting with water a commercially available solution of a basic aluminium chloride (as in Example 9). The solution is then heated at a temperature of 50° to 140° C. so as to modify the distribution of the polymeric species within such solution in such manner that the modified basic aluminium chloride has at least 20%, preferably at least 25%, of the aluminium contained in the Band III fraction as determined by a chromatographic analytical procedure described in the patent. The products obtained having such high contents of aluminium in the Band III fraction have superior antiperspirant activity. Powdered forms of the improved basic aluminium chlorides are obtained by drying the heat-treated solutions.

In EP-A-No. 191 628 (Application No. 86 300916.3) (Unilever) there is described a simplified process for making a powder of a basic aluminium chloride having a high proportion of the aluminium in the Band III fraction without the need to heat-treat a pre-formed solution of a basic aluminium chloride. In the process of said application a powdered basic aluminium chloride having a high content of aluminium in the Band III fraction is prepared directly.

More particularly, EP-A-No. 191 628 relates to a process of making a basic aluminium chloride in powder form having an aluminium:halogen molar ratio of from 1.7 to 2.2:1 and having at least 20% of the aluminium contained in the Band III fraction which process comprises the steps of:

(a) dissolving metallic aluminium in an aqueous starting solution of an aluminium compound selected from aluminium chloride and aluminium bromide, said starting solution being held at a temperature of about 50° C. to about 105° C., preferably 50° C. to 95° C., for a time just long enough to dissolve sufficient aluminium to produce an aqueous solution of a final basic aluminium chloride having an aluminium:chloride molar ratio in the range 1.7:1 to 2.2:1, the concentration of the aluminium in the starting solution and the amount of aluminium dissolved being such that the aluminium concentration in the solution of the final basic aluminium chloride is from 0.8% to 6.75% by weight and said final basic aluminium chloride having at least 20% of the aluminium contained in the Band III fraction; and (b) drying the solution of the final basic aluminium chloride so as to give the final basic aluminium chloride in the form of an hydrated powder having at least 20% of the aluminium contained in the Band III fraction.

The previously described methods have the disadvantage that either they are conducted in high concentration but produce a low proportion of polymers in the Band III fraction or if they do produce materials having a relatively high proportion of aluminium in the Band III fraction, the process must be conducted in relatively low concentration which is relatively inconvenient and expensive, particularly if a powdered product is required.

It is an object of the present invention to provide an improved process for making a powder of a basic aluminium chloride having a high Band III fraction without the need to heat-treat a pre-formed solution of a basic aluminium chloride. In the process of the invention a solution having a high Band III fraction is prepared directly and in higher concentration than in EP-A-No. 191 628. The solution so prepared is dried to a powder by a suitable method e.g. freeze-drying or spray-drying.

The process of the present invention is based on the discovery that in the preparation of solutions of basic aluminium chlorides by the dissolution of aluminium in an aqueous solution of aluminium chloride or a basic aluminium chloride, a solution having a relatively high concentration of the final basic aluminium chloride with, surprisingly, a relatively high Band III fraction can be prepared provided the reaction is carried out sufficiently rapidly.

According to the present invention there is provided a process of making a basic aluminium chloride in powder form having an aluminium: chlorine molar ratio of from 1.7 to 2.2:1 and having a Band III fraction of at least 20%, which process comprises the steps of:

(a) rapidly dissolving metallic aluminium powder in an aqueous starting solution of aluminium chloride or a basic aluminium chloride having an aluminium:chlorine molar ratio up to 1.8:1, preferably in the range 0.9:1 to 1.5:1, said starting solution being held at a temperature of about 50° C. to about 105° C. for a time just long enough to dissolve sufficient aluminium to produce an aqueous solution of a final basic aluminium chloride having an aluminium:chlorine molar ratio in the range 1.7 to 2.2:1, provided that in the case where the starting aluminium compound is a basic aluminium chloride the amount of aluminium dissolved is such that the final basic aluminium chloride has an aluminium:chlorine molar ratio which exceeds by at least about 0.3, preferably at least 0.4, that of the starting basic aluminium chloride, the concentration of the aluminium in the starting solution and the amount of aluminium dissolved being such that the aluminium concentration in the solution of the final basic aluminium chloride is from 7.5 to 13% by weight, and the reaction being carried out in such manner that the metallic aluminium powder is dissolved so rapidly that said final basic aluminium chloride has a Band III fraction of at least 20%, preferably at least 25%; and (b) drying the solution of the final basic aluminium chloride so as to give the final basic aluminium chloride in the form of a hydrated powder having a Band III fraction of at least 20%, preferably at least 25%.

Characterisation of materials containing species differing in size by means of size exclusion chromatography is generally known. The size exclusion chromatographic procedures for characterising the basic aluminium compounds of this invention will now be described.

The analytical procedure is performed on a stainless steel column of dimensions 25 to 30 cm high and of 7 mm internal diameter packed with porous silica of nominal particle size 5 microns and pore size of 60 Angstroms, which silica has been deactivated by silylation to eliminate adsorption and unwanted ionic effects in size exclusion separations. A suitable silica is that available commercially as LiChrosorb RP-2. The silica employed by the Applicants in deriving analytical data given herein had a cumulative undersize particle size distribution by weight of 10% less than 5 microns, 50% less than 6 microns and 90% less than 7 microns.

The column is fitted at the bottom with a zero dead volume fitting containing a 2 micron mesh stainless steel bed support. The silica is packed into the column by the high pressure slurry method (see Practical High Performance Liquid Chromatography, Edited by C F Simpson, 1976, Appendix II), using dichloromethane as the packing medium.

After packing, the column is capped with another zero dead volume fitting containing a 2 micron stainless steel mesh. The packed column is then eluted with 200 ml of methanol at a flow rate of about 10 ml/min, using a high pressure pump, to consolidate the bed and wash out the packing medium.

A differential refractive index monitor (e.g. Waters R401) is used to detect sample fractions as they are eluted. It is linked to a pen recorder to provide a chromatogram and to an integrator which measures the elution times of the fractions and the relative chromatographic band areas. The integrator is required to measure areas of bands not resolved to the baseline by dropping perpendiculars from the lowest point of the valleys separating the bands to the baseline.

The column packing should be tested according to the procedure of Bristow & Knox (Chromatographia, Volume 10, No 6, June 1977, pp 279-89) for reverse phase materials and should generate at least 20,000 plates/meter for the test component phenetole.

To prepare test solutions of the materials for analysis those already in solution are used undiluted unless the aluminium concentration exceeds 2.5% by weight in which case they are diluted with deionized water to give a solution containing 2.5% by weight aluminium. Solid materials (e.g. spray dried powders) are dissolved in deionized water to give a solution containing 2.5% by weight aluminium. Solids or solutions which do not disperse readily on shaking are dispersed by treatment in an ultrasonic bath (e.g. Sonicor Model No. SC-150-22TH) for 5 minutes. The solutions prepared in this way are filtered through a 25 mm diameter membrane having a pore size of 0.025 micrometers to give the test solutions. The preparation of a test solution is carried out immediately prior to application of a sample to the column.

A sample of the test solution containing about 2 to 4 micromoles of aluminium is applied to the top of the column by means of a precision micro-liter syringe and a sample injection port. The sample is eluted with a $1 \times 10^{-2}$M aqueous nitric acid solution at a flow rate of 1.0ml/min using a high pressure pump.

Eluted fractions of a test sample are characterised by means of the ratio of their retention times to the retention time of the totally included species. In the case of basic aluminium chlorides the totally included species arises from hydrochloric acid (which is present in solutions of basic aluminium chlorides) as can be shown by comparison of its retention time with that of a sample of hydrochloric acid. Using columns satisfying the above description and employing a standard solution of a basic aluminium chloride prepared as described below, the Applicants have obtained separation into four aluminium-containing fractions having relative retention times within the ranges indicated.

|  | Band I | Band II | Band III | Band IV |
| --- | --- | --- | --- | --- |
| Relative Retention Time Range | 0.62–0.70 | 0.71–0.75 | 0.76–0.82 | 0.83–0.97 |

The standard basic aluminium chloride solution is prepared as a solution containing 12.5% by weight aluminium from 19.1 g of aluminium chloride hexahydrate, 10.5 g of 99.9% pure aluminium wire (0.76 mm diameter, cut in approximately 1 cm lengths and degreased by washing in acetone) and 70.4 g of deionised water. The mixture is stirred and heated at 80°–90° C. under a reflux condenser until all of the aluminium is dissolved. Any traces of insoluble solids are removed by filtration to give a clear solution.

When this material is analysed by the size exclusion chromatographic procedure described herein, there are obtained the following four fractions having typical relative retention times and chromatographic band areas expressed as percentages of the total chromatographic band area representing aluminium-containing material.

|  | Band I | Band II | Band III | Band IV |
| --- | --- | --- | --- | --- |
| Relative Retention Time | 0.65 | 0.73 | 0.79 | 0.91 |
| Band Area % of total aluminium band area | 39 | 51 | 4 | 6 |

It will be appreciated by those skilled in the art that mechanisms of separation other than the principal mechanism of size exclusion may play a part in this type of chromatography. Examples of the processes would be adsorption effects and hydrodynamic effects. Thus although it is possible for a given column and constant operating conditions to lead to invariable relative retention times, minor variations in particle size range and pore size distribution of the column packing material may lead to slight differences in relative retention times.

Basic aluminium chlorides produced by the process of the present invention are characterised by the proportion of the area of Band III of their size exclusion chromatogram expressed as a percentage of the sum of all the areas of the Bands corresponding to the aluminium—containing fractions. Thus the percentage of the Band III fraction is given by the expression:

$$\% \text{ Band III fraction} = \frac{\text{Area of Band III}}{\text{Sum of all the areas of the aluminium − containing bands}} \times 100$$

The general reaction of aluminium with an aqueous solution of an aluminium chloride is, as indicated, well-known. When the starting solution is an aqueous solution of aluminium chloride, this may be preformed by dissolving aluminium in an aqueous hydrochloric acid solution of appropriate concentration. When the starting solution is an aqueous basic aluminium chloride solution, this may be formed by dissolving a basic aluminium chloride in solid form in water, or by diluting with water a relatively concentrated solution of the basic aluminium chloride, a number of which basic aluminium chlorides are readily available commercially.

An essential feature of the process of the invention for making a basic aluminium chloride in powder form with high antiperspirant activity is the use of proportions of reactants such that when the desired final basic aluminium chloride is formed, usually at the point when substantially all the aluminium has dissolved, the aluminium concentration of that solution is relatively high, i.e. from 7.5 to 13% by weight, preferably 8 to 12.5%, more preferably 9 to 11%. At concentrations above about 13% the product tends to become very viscous and the reaction slows down in the later stages. The reaction time becomes so critical at these very high concentrations that attainment of the required reaction time is virtually impossible. Reactions as are currently commercially practised do not lead to products having a high Band III fraction percentage. A combination of factors, the form of the aluminium used and the reaction temperature and concentration result in a reaction time which is too prolonged to meet the critical requirements of the present invention. As described below, these are particularly critical at the high concentrations and temperatures at which, for economic reasons, current commercial reactions are carried out.

The rapid reaction which is a crucial feature of the process of the present invention can be achieved by using aluminium in the form of aluminium powder of sufficient reactivity. It is necessary to use a finely divided powders and those powders passing a 200 mesh sieve are preferred. When using the more reactive grades of aluminium powder it is not necessary to employ a catalyst and in any case known toxic catalysts such as thallium should be avoided since the final product is intended for personal use. The addition of the aluminium powder to the reaction mixture should be carried out as quickly as is consistent with a safely and accurately controlled reaction. The reaction is most conveniently carried out at atmospheric pressure although elevated pressures, for example, can be used.

As emphasised above, the essence of the present invention is to dissolve aluminium in an aluminium chloride solution or a basic aluminium chloride solution sufficiently quickly that the Band III fraction of the resulting solution of the basic final aluminium chloride is at least 20%, preferably at least 25%, and more preferably at least 30%. The reaction time is critical and its criticality is both concentration- and temperature- dependent. Generally speaking, reactions starting with aluminium chloride and carried out at a temperature of about 90° C. or higher and at a final aluminium concentration of about 12% should be completed within about 5 hours. Reactions starting from aluminium dichlorhydrate or sesquichlorhydrate will be correspondingly shorter. As the temperature and/or the aluminium concentration of the reaction mixture are reduced the reaction time may be somewhat extended while still obtaining a high Band III fraction percentage. Illustrations of the effect of varying the various parameters may be seen in the Examples given hereafter.

These general considerations also apply to reactions using as starting material a basic aluminium chloride such as aluminium dichlorhydrate or aluminium sesquichlorhydrate. In these cases there is an additional variable, namely the aluminium: chlorine ratio of the starting material. Generally, the formation of product containing a higher Band III fraction is favoured by selection of a starting material with a lower Al:chlorine ratio, e.g. about 1:1 or below.

There is therefore clearly a complex relationship between reaction temperature, final aluminium concentration, reaction time and starting Al:chlorine ratio and the Band III fraction of the final product of any given Al: chlorine ratio. The effects of these factors can be clearly seen from the Tables in the Examples given hereinafter.

Suitable finely-divided aluminium powders for use in the process of the invention are, for example, the atomised aluminium powders sold by The Aluminium Powder Company Limited, England, under the trade name Alpoco. Various grades are available, for instance the grade designated 200/Dust which designation indicates that the particle size ranges from that passing a 200 mesh standard sieve down to dust. A suitable finer grade is that designated 350/Dust.

The product of the present invention may have an Al:chlorine ratio lying between 1.7 and 2.2. For antiperspirant use the most preferred range is 1.9–2.1 as it is within this range that products of lowest irritancy and satisfactory antiperspirancy are obtained. Also of particular interest is the range lying between 1.7 and 1.9, for which range the materials are called aluminium sesquichlorhydrates. For the purposes of the present invention, products of lower Al:chlorine ratio have the advantage that for a given set of reaction conditions they can be made more rapidly than those of higher Al:chlorine ratio. The reduced heating time is advantageous in the preparation of products having a Band III fraction in excess of 20%.

In the direct preparative procedure of the invention, under some conditions products containing a high Band III fraction contain a substantial proportion of this component in the form of a polymer having a characteristic line in the $^{27}$Al NMR spectrum. This line is 62.5 ppm downfield from the resonance of $Al^{3+}(6H_2O)$. This line has been attributed to the presence of a complex ion $[Al_{13}O_4(OH)_{24}(H_2O)_{12}]^{7+}$ by Akitt et al (J.C.S. Dalton Transactions 1972 p604) the structure of which was first established by G Johannson (Acta Chem Scand 1960 Vol 14 p771). This ion has been subsequently referred to as the $Al_{13}O_{40}$ ion by Schonherr et al (Zeitschrift fur Anorganischen und Allgemeinen Chemie, 502, 113–122 (1983)).

The quantitative determination of the percentage of aluminium present in the $Al_{13}O_{40}$ ion will now be described.

The essence of the measurement is the comparison of the band area of the sharp band from the central Al atom of the $Al_{13}O_{40}$ species [$\delta=62.5$ ppm with respect to $Al^{3+}$ hexaaquo $=0$] with the area of the aluminate ion band [$\delta=80$ ppm]. The aluminate standard (concentration about 0.1M) is contained in a sealed 5 mm NMR tube which is held concentrically inside a 10 mm NMR tube. The annular space between the two tubes is filled with analyte solution. The aluminate standard is freshly made up and calibrated for each series of experiments.

For calibration purposes, this annular space is filled with an aqueous solution containing a known concentration (e.g. 0.02M) of an aluminium salt, such as Analar aluminium nitrate. From the $^{27}Al$ NMR spectrum of this system, the area of the aluminate ion band ($\delta=80$ ppm) is compared with that of the $Al^{3+}$ band ($\delta=0$ ppm), the effective concentration of aluminium in the aluminate-containing tube being given by the equation:

$$M_s = \frac{I_s}{I_A} \times M_A$$

where
- $M_s$ is the effective molar concentration of aluminium in the aluminate solution
- $M_A$ is the molar concentration of aluminium in the $Al(NO_3)_3$ solution
- $I_s$ is the area of the aluminate band
- $I_A$ is the area of the $Al^{3+}$ band from $Al(NO_3)_3$.

Thus $M_s$ is the 'calibration factor' of the sealed tube of aluminate solution, and the use of this tube, as indicated above, with subsequent analyte solutions of unknown composition will allow the amount of aluminium associated with any particular sharp spectral band from the analyte solution to be determined.

Measurement of the central aluminium band of $Al_{13}O_{40}$ species determines only one thirteenth of the aluminium content (the other 12 aluminium atoms produce a resonance band which is too broad to be measured accurately). Hence the total amount of aluminium present in the $Al_{13}O_{40}$ species is obtained by multiplying the area of the central band ($\delta=62.5$ ppm) by 13.

The concentration of aluminium thus calculated to be present in the $Al_{13}O_{40}$ species is expressed as a percentage of the total aluminium concentration of the analyte solution which if unknown may be determined e.g. by atomic absorption spectrometry.

All NMR measurements were carried out using a Bruker W.M.360 spectrometer with a probe free from background aluminium signal. Sample tubes were made from quartz which is also free from background aluminium signal. The aluminium concentration of the analyte solutions whose $Al_{13}O_{40}$ concentration was to be determined was in the range 0.8% to 2.7% by weight. In the process of the present invention, the Band III fraction may contain a variable proportion of the $Al_{13}O_{40}$ species, depending on conditions. This proportion is not critical.

The solutions of this invention, which have more than 20% Band III, are generally rather unstable, particularly those of higher concentration. It is therefore necessary to dry them without undue delay by a suitable process such as freeze-drying or spray-drying.

The following Examples illustrate the invention. Band III fractions are given in the Tables. The references in parentheses (e.g. 534Z) are the applicant's laboratory codes for the respective reactions described.

EXAMPLE 1 (534Z)

Aluminium chloride hexahydrate (45.3 g) was dissolved in water (179.4 g). This solution was placed in a conical flask fitted with a thermometer and air-condenser. A magnetic stirrer-bar was added and the temperature raised to 90° with stirring on a magnetic stirrer-hotplate. Atomised aluminium powder (Alpoco 350/Dust), 99.7% pure, (25.3 g) was added in portions. The first portion (5 g) was added during the warm-up stage and the remainder was added as quickly as was consistent with a controlled reaction, and maintenance of the temperature at 90°±5° C. The flask was cooled with water if necessary. The reaction was completed in 4.5 hours from the start of the initial heating. The solution was filtered without delay through a Whatman 541 filter-paper and a sample frozen in an alcohol-bath at −55° C. prior to freeze-drying using a Lyolab BII freeze-dryer (Life Science Labs Ltd). The powder was redissolved and subjected to chromatographic analysis.

EXAMPLE 2 (540F)

Example 1 was repeated using Alpoco 200/Dust, 99.7% pure, save that the reaction was carried out at 75° C. at which temperature it was completed in 7.5 hours.

EXAMPLE 3 (533B)

Aluminium chloride hexahydrate (35.2 g) was dissolved in water (195.1 g). This solution was placed in a conical flask fitted with a thermometer and air-condenser. A magnetic stirrer-bar was added and the temperature raised to 90° C. with stirring on a magnetic stirrer-hotplate. Atomised aluminium powder (Alpoco 350/Dust), 99.7% pure (19.7 g) was added in portions. The temperature of the reaction was maintained at 90°±5° C. by heating or cooling in a water-bath as appropriate. The reaction was completed in 5 hours. The solution was filtered without delay through a Whatman 541 filter-paper and a sample frozen in an alcohol-bath at −55° C. prior to freeze-drying using a Lyolab BII freeze dryer (Life Sciences Labs Ltd). The powder was redissolved and subjected to chromatographic analysis.

EXAMPLE 4 (539Q)

Aluminium chloride hexahydrate (30.2 g) was dissolved in water (203.0 g). This solution was placed in a conical flask fitted with a thermometer and air-condenser. A magnetic stirrer-bar was added and the temperature raised to 75° C. with stirring on a magnetic stirrer-hotplate. Atomised aluminium powder (Alpoco 200/Dust), 99.7% pure, (16.9 g) was added in portions. The first portion (5 g) was added during the warm-up stage and the remainder added as quickly as was consistent with a controlled reaction and maintenance of the temperature at 75°±4° C. The flask was cooled by plunging in cold water if necessary. The reaction was completed in 7.5 hours. The solution was filtered without delay through a Whatman 541 filter-paper and a sample frozen in an alcohol-bath at −55° C. prior to freeze-drying using a Lyolab BII freeze-dryer (Life Science Labs Ltd). The powder was redissolved and subjected to chromatographic analysis.

EXAMPLE 5 (533I)

Example 4 was repeated using Alpoco 350/Dust, 99.7% pure, save that the reaction was carried out at 90° C. at which temperature the reaction was completed in 5 hours.

EXAMPLE 6 (537K)

In this example the procedure of Example 4 was again followed save that all the aluminium was added at once and the temperature of reaction was 55° C. at which temperature the reaction was completed in 12 hours.

The following examples which are included in European Patent Application No. 86 300916.3 as comparative Examples B, C and E are included in this specification also for comparative purposes.

Example B (275F)

Aluminium chloride hexahydrate (45.27 g) was dissolved in water (179.4 g). This solution was placed in a conical flask fitted with a thermometer and air-condenser. A magnetic stirrer bar and a drop of mercury were added and the temperature raised to 75° C. on a magnetic stirrer hotplate. Degreased aluminium foil (25.29 g) was added in approximately two equal portions, each portion being added as the dissolution of the previous one was nearly complete. The reaction mixture was stirred and maintained at 75° C.±5° until all the aluminium had dissolved which required 5 days. Evaporation losses were made good by the addition of deionised water, the solution filtered and a sample taken for analysis.

Example C (274D)

This comparative Example was carried out as in comparative Example B save that the reaction temperature was 55° C.. The time required for all the aluminium to dissolve was 8 days.

Example E (280N)

Aluminium chloride hexahydrate (45.27 g) was dissolved in water (179.4 g). This solution was placed in a conical flask fitted with a thermometer and air-condenser. A magnetic stirrer bar was added and the temperature raised to 90° C. on a magnetic stirrer hotplate. Degreased aluminium foil (25.29 g) was added in approximately ten equal portions, each successive portion being added as the dissolution of the previous one was nearly complete. The reaction mixture was stirred and maintained at 90° C.±5° until all of the aluminium had dissolved which required 5 days. Evaporation losses were made good by the addition of deionised water, the solution filtered and a sample taken for analysis.

Examples 7 and F further illustrate the effect of the reaction time on the Band III fraction of the final product.

EXAMPLE 7 (544G)

Example 3 was repeated using Alpoco 200/Dust, 99.97% pure, grade save that the addition of aluminium was controlled so as to result in a reaction time of 7.8 hours instead of 5 hours as in Example 3. A small amount of unreacted aluminium was removed by filtration.

Example F (544D)

Example 1 was repeated save that the aluminium powder used was Alpoco 200/Dust, 99.97% pure, grade and the addition of aluminium was controlled so as to result in a reaction time of 7.8 hours instead of 4.5 hours as in Example 1. A small amount of unreacted aluminium was removed by filtration.

The following further Examples 8 to 17 illustrate the use of a starting solution of a basic aluminium chloride. In Examples 8 to 11 the basic aluminium chloride is an aluminium dichlorhydrate and in Examples 12 to 17 the basic aluminium chloride is an aluminium sesquichlorhydrate.

EXAMPLE 8 (562W)

Aluminium dichlorhydrate powder (52.6 g) having an Al:Cl molar ratio of 1.1:1 and having an aluminium content of 20.4% was dissolved in water (187.9 g). This solution was placed in a conical flask fitted with a thermometer and air condenser. A magnetic stirrer bar was added and the temperature raised to 90° C. with stirring on a magnetic stirrer-hotplate. Aluminium powder (Alpoco 200/Dust) 99.7% pure (9.5 g) was added during the warm-up stage and the temperature was maintained at 90°±5° C. The flask was cooled with water if necessary. The reaction was completed in 2hr 15mins. The solution was filtered to give a clear solution.

EXAMPLE 9 (559U)

Example 8 was repeated using aluminium dichlorhydrate (78.8 g), water (156.9 g) and aluminium powder (14.3 g). The reaction was completed in 2 hours.

EXAMPLE 10 (561F)

Example 8 was repeated using aluminium dichlorhydrate (52.6 g), water (187.9 g) and aluminium powder (9.5 g), save that the reaction was carried out at 75° C. at which temperature it was completed in 3 hrs 45 mins.

EXAMPLE 11 (561L)

Example 8 was repeated using aluminium dichlorhydrate (39.4 g), water (78.5 g) and aluminium powder (7.1 g) save that the reaction was carried out at 75° C., at which temperature it was completed in 3hrs 15 mins.

EXAMPLE 12 (552R)

An aqueous solution (127.8 g) of an aluminium sesquichlorhydrate having an Al:Cl molar ratio of 1.4:1, the solution having an aluminium content of 11.0%, was diluted with water (116.1 g). This solution was placed in a conical flask fitted with a thermometer and air condenser. A magnetic stirrer-bar was added and the temperature raised to 90° C. with stirring on a magnetic stirrer-hotplate. Aluminium powder (Alpoco 200/Dust) 99.7% pure (6.1 g) was added in portions. The first portion (1.3 g) was added during the warm-up stage and the remainder was added as quickly as was consistent with a controlled reaction, and maintenance of the temperature at 90°±5° C. The reaction was completed in 2 hours 45 mins. The product was filtered to give a clear solution.

EXAMPLE 13 (551M)

Details of the above Examples 1 to 7 are summarised in Table 1, Comparative Examples B, C, E and F in Table 2, Examples 8 to 11 in Table 3 and Examples 12 to 17 in Table 4.

TABLE 1

| Example | Final Al/Cl Molar Ratio | Final Al concentration (weight %) | Reaction Temp. (°C.) | Reaction Time (hr) | Band III fraction (%) | % Al in Al$_{13}$ species |
|---|---|---|---|---|---|---|
| 1 | 2.0 | 12.1 | 90 | 4.5 | 37 | 23 |
| 2 | 2.0 | 12.1 | 75 | 7.5 | 40 | 25 |
| 3 | 2.0 | 9.4 | 90 | 5 | 43 | 31 |
| 4 | 2.0 | 8.1 | 75 | 7.5 | 60 | 53 |
| 5 | 2.0 | 8.1 | 90 | 5 | 63 | 44 |
| 6 | 2.0 | 8.1 | 55 | 12 | 89 | 69 |
| 7 | 1.9 | 8.9 | 90 | 7.8 | 24 | |

TABLE 2

| Example | Final Al/Cl Molar Ratio | Final Al concentration (weight %) | Reaction Temp. (°C.) | Reaction Time | Band III fraction (%) |
|---|---|---|---|---|---|
| B | 2.0 | 12.1 | 75 | 5 days | 4 |
| C | 2.0 | 12.1 | 55 | 8 days | 8 |
| E | 2.0 | 12.1 | 90 | 5 days | 7 |
| F | 1.7 | 11.4 | 90 | 7.8 hours | 11 |

TABLE 3

| Example | Final Al/Cl Molar Ratio | Final Al concentration (weight %) | Reaction Temp. (°C.) | Reaction Time | Band III fraction (%) |
|---|---|---|---|---|---|
| 8 | 2.0 | 8.1 | 90 | 2 hr 15 min | 56 |
| 9 | 2.0 | 12.1 | 90 | 2 hr | 37 |
| 10 | 2.0 | 8.1 | 75 | 3 hr 45 min | 60 |
| 11 | 2.0 | 12.1 | 75 | 3 hr 15 min | 47 |

TABLE 4

| Example | Final Al/Cl Molar Ratio | Final Al concentration (weight %) | Reaction Temp. (°C.) | Reaction Time | Band III fraction (%) |
|---|---|---|---|---|---|
| 12 | 1.95 | 8.1 | 90 | 2 hr 45 min | 36 |
| 13 | 1.86 | 12.1 | 90 | 2 hr 45 min | 21 |
| 14 | 1.86 | 8.1 | 75 | 3 hr 35 min | 39 |
| 15 | 1.72 | 12.1 | 75 | 3 hr 30 min | 33 |
| 16 | 1.87 | 8.1 | 55 | 8 hr 50 min | 37 |
| 17 | 1.88 | 12.1 | 55 | 9 hr | 38 |

Example 12 was repeated using aluminium sesquichlorhydrate (191.7 g), water (49.1 g) and aluminium powder (9.2 g). The reaction was completed in 2 hours 45 mins.

EXAMPLE 14 (554A)

Example 12 was repeated save that it was carried out at 75° C. at which temperature it was completed in 3 hours 35 mins.

EXAMPLE 15 (554T)

Example 13 was repeated save that it was carried out at 75° C. at which temperature it was completed in 3 hours 30 mins.

EXAMPLE 16 (556X)

Example 12 was repeated save that it was carried out at 55° C., at which temperature it was completed in 8 hours 50 mins.

EXAMPLE 17 (553J)

Example 13 was repeated save that it was carried out at 55° C., at which temperature it was completed in 9 hours.

EXAMPLE 18 (624Z)

Aluminium chloride hexahydrate (29.81 g) was dissolved in water (206.53 g). The solution was placed in a conical flask fitted with a thermometer and air-condenser. A magnetic stirrer-bar was added and the temperature raised to 90° C. on a magnetic stirrer-hotplate. Atomised aluminium powder (Alpoco 200/Dust), 99.7% pure (13.66 g) was added in portions. The first portion, about 3.5 g, was added during the warm-up stage and the remainder was added as quickly as was consistent with a controlled reaction, and maintenance of the temperature at 90°±5° C. The flask was cooled with water if necessary. The reaction was completed in 2hr 35 min. The cooled solution was filtered through a Whatman 41 filter paper. When subjected to chromatographic analysis the solution was shown to have a Band III fraction of 47%.

EXAMPLE 19 (620C)

Example 1 was repeated using 38.999 g of aluminium chloride hexahydrate, 193.15 g of water, and 17.86 g of aluminium powder. The reaction was completed in 2hr 50min. Chromatographic analysis of the product showed that it had a Band III fraction of 25%.

EXAMPLE 20 (726F)

Aluminium chloride hexahydrate (119.24 g) was dissolved in water (814.08 g). The solution was placed in a conical flask fitted with a thermometer and air-condenser. A magnetic stirrer-bar was added and the temperature raised to 90° C. on a magnetic stirrer-hotplate. Atomised aluminium powder (Alpoco 200/Dust), 99.7% pure (66.64 g) was added in portions. The first portion, about half, was added during the warm-up stage and the remainder was added as quickly as was consistent with a controlled reaction, and maintenance of the temperature at 90°±5° C. The flask was cooled by plunging in cold water if necessary. The reaction was completed in 3hr 10 mins, and the solution was cooled and filtered through Whatman GFC paper. This solution was pooled with the product of two other identical reactions made at the same time. Drying was carried out using a Niro Mobile Minor spray drier, adjusted to the following operational conditions.

| | |
|---|---|
| inlet temperature | 300° C. |
| outlet temperature | 105° C. |
| input flowrate | 65 ml/min |

Chromatographic analysis of the dry product showed that it had a Band III fraction of 56%. The amount of aluminium contained in the Al13 species was 42% of the total aluminium.

EXAMPLE 21 (720E)

Example 3 was repeated using aluminium chloride hexahydrate (203.72 g), water (807.45 g) and aluminium powder (113.82 g). The reaction was completed in 3hr 10 min and the cooled filtered solution was pooled with the product of another identical reaction made at the same time. The spray drying was carried out under the following operational conditions

| | |
|---|---|
| inlet temperature | 300° C. |
| outlet temperature | 105° C. |
| input flowrate | 60 ml/min. |

Chromatographic analysis of the dry product showed that it had a Band III fraction of 32%. The amount of aluminium contained in the $Al_{13}$ species was 21% of the total aluminium.

EXAMPLE 22

Aluminium chloride hexahydrate (35.2 g) was dissolved in water (195.1 g). This solution was placed in a conical flask fitted with a thermometer and air-condenser. A magnetic stirrer-bar was added together with a portion of aluminium powder. The temperature was raised to 90° C. on a magnetic stirrer-hotplate and the reaction mixture maintained at 90° C.±5° C. by cooling or warming as appropriate. When the original energetic reaction had subsided, further portions of aluminium were added successively to maintain a controlled reaction at 90°±5° C. By variation of the grade of aluminium powder and/or the size and frequency of additions the total time for dissolution of a total weight of 19.7 g of aluminium powder was varied, as shown in the table. The final aluminium concentration was about 9.4%. Data are summarised below in Table 5.

TABLE 5

| Experiment | | Grade of Aluminium | Reaction Time | Band III fraction (%) |
|---|---|---|---|---|
| 22A | (741I) | Alpoco 200/D,99.7% | 2 hr 5 min | 63 |
| 22B | (533B) | Alpoco 350/D,99.7% | 5 hr | 43 |
| 22C | (740U) | Alpoco 200/D,99.7% | 6 hr 30 min | 26 |
| 22D* | (544G) | Alpoco 200/D,99.97% | 8 hr | 22 |

*Final Al:Cl ratio was about 1.9

The data show the effect of reaction time on the Band III fraction.

Comparative Example G (584I)

Aluminium chloride hexahydrate (22.64 g) was dissolved in water (89.7 g). This solution was placed in a conical flask fitted with a thermometer and air-condenser. A magnetic stirrer-bar and aluminium powder (Aldrich Gold Label 99.99%, 100 mesh) (12.65 g) were added. The mixture was heated and stirred until the exothermic reaction began (about 70° C.). The temperature was controlled at 90°±5° C. by warming or cooling as necessary. When after 6½ hours the aluminium was substantially dissolved, the slight grey residue was removed by filtration to give a clear solution. Chromatographic analysis showed that it had a Band III fraction of 11%.

Comparative Example H (583R)

Aluminium chloride hexahydrate (45.27 g) was dissolved in water (179.4 g). This solution was placed in a conical flask fitted with a thermometer and air condenser. A magnetic stirrer-bar and aluminium powder (B.D.H. Laboratory Reagent, Coarse) (25.3 g) were added. The mixture was heated and stirred until the exothermic reaction began (about 60° C.). The temperature was controlled at 90°±5° C. by warming or cooling as necessary. When, after 5½ hours the aluminium was substantially dissolved, the solution was filtered. Chromatographic analysis showed that it had a Band III fraction of 18%.

Comparative Example J (575H)

Aluminium chloride hexahydrate (45.3 g) was dissolved in water (179.4 g). This solution was placed in a conical flask fitted with a thermometer and air-condenser. A magnetic stirrer-bar and aluminium powder (FISONS Laboratory Reagent, grease-free, coarse) 8.4 g were added. The mixture was heated and stirred until the exothermic reaction began (about 50° C.). The temperature was controlled at 90°±5° C. by warming or cooling as necessary. When the reaction moderated a further portion of aluminium powder (8.4 g) was added and the temperature again maintained at 90°±5° C. The remaining aluminium (total 25.3 g) was added when this reaction subsided. When all the aluminium had dissolved, the mixture was cooled and filtered through a Whatman 541 filter-paper. Chromatographic analysis of the solution showed that it had a Band III fraction of 13%. The total reaction time was 9 hours 15 minutes.

The above Comparative Examples G, H and J show that when using an inappropriate grade of aluminium powder the reaction did not proceed sufficiently rapidly.

EXAMPLE 23

A number of experiments were carried out in the following general manner which involved dissolving aluminium powder in an aqueous solution of aluminium chloride to produce a final solution having an aluminium content of about 12.1%. Aluminium chloride hexahydrate was dissolved in water and the solution placed in a conical flask fitted with a thermometer and air condenser. A magnetic stirrer-bar and some or all of the aluminium powder added. The mixture was heated and stirred until the reaction began and the temperature was controlled at 90°±5° C. by warming or cooling as necessary. By variation of the grade of aluminium powder and/or the size and frequency of additions of the powder the total time for dissolution of the aluminium powder was varied. Data relating to these experiments are given in Table 6. The data include some from previously described examples.

TABLE 6

| Example | | Grade of Aluminium | Reaction Time | Band III fraction (%) |
|---|---|---|---|---|
| 23A | (581L) | Alpoco 200/D, 99.7% | 2 hr 20 min | 41 |
| 23B | (560B) | Alpoco 200/D, 99.7% | 3 hr 45 min | 36 |
| 23C | (558E) | Alpoco 200/D, 99.7% | 3 hr 15 min | 34 |
| 23D | (720E) | Alpoco 200/D, 99.7% | 3 hr 10 min | 33 |
| 23E | (617U) | Alpoco 200/D, 99.7% | 2 hr 40 min | 27 |
| 23F | (584S) | Alpoco 200/D, 99.7% | 6 hr 30 min | 18 |
| H | (583R) | BDH. Lab. Reagent, coarse | 5 hr 30 min | 18 |
| 23G | (579F) | BDH. Lab. Reagent, coarse | 5 hr 15 min | 18 |
| J | (575H) | Fisons Lab Reagent coarse | 9 hr 15 min | 13 |
| G | (5841) | Aldrich, 100 mesh, 99.99% | 6 hr 30 min | 11 |

These data again show the general effect that increase in the reaction time results in lower Band III values.

What is claimed is:

1. Process of making a basic aluminum chloride in powder form having an aluminum:chloride molar ratio of from 1.7 to 2.2:1 and having a Band III fraction of at least 20% which comprises the steps of:
    (a) rapidly dissolving metallic aluminum powder which passes a 200 mesh sieve in an aqueous starting solution of aluminum chloride or, a basic aluminum chloride, having an aluminum:chloride molar ratio of up to 1.8:1, said starting solution being held at a temperature of about 50 degrees C. to about 105 degrees C. for a time just long enough to dissolve sufficient aluminum to produce an aqueous solution of a final basic aluminum chloride having an aluminum:chloride molar ratio in the range of 1.7 to 2.2:1, provided that in the case where the starting aluminum compound is a basic aluminum chloride the amount of aluminum dissolved is such that the final basic aluminum chloride has an aluminum:chlorine molar ratio which exceeds by at least 0.3 that of the starting basic aluminum chloride, the concentration of the aluminum in the starting solution and the amount of aluminum dissolved being such that the aluminum concentration in the solution of the final basic aluminum chloride is from 7.5% to 13% by weight, and the reaction being carried out within 5 hours and in such manner that the metallic aluminum powder is dissolved so rapidly that said final basic aluminum chloride has a Band III fraction of at least 20%; and
    (b) drying the solution of the final basic aluminum chloride so as to give the final basic aluminum chloride in the form of a hydrated powder having a Band III fraction of at least 20%.

2. Process as claimed in claim 1 wherein said starting solution is an aqueous solution of aluminium chloride.

3. Process as claimed in claim 1, wherein said starting solution is an aqueous solution of a basic aluminium chloride having an aluminium: chlorine molar ratio of 0.9 to 1.5:1.

4. Process as claimed in claim 1 wherein the hydrated powder of the final basic aluminium chloride has a Band III fraction of at least 25%.

5. Process as claimed in claim 4 wherein the hydrated powder of the final basic aluminium chloride has a Band III fraction of at least 30%.

6. Process as claimed in claim 1 wherein the final basic aluminium chloride powder has an aluminium: chlorine molar ratio of 1.9 to 2.1:1.

7. Process as claimed in claim 1 wherein the drying of the solution of the final basic aluminium chloride in step (b) is carried out by spray drying or freeze drying.

8. Process as claimed in claim 1 wherein in step a) the reaction is conducted at about 90° C. to produce a final basic aluminium chloride solution having an aluminium concentration of about 12% by weight and the reaction time is less than 5 hours.

9. Process as claimed in claim 1 wherein the aluminium powder is atomised aluminium powder.

* * * * *